United States Patent [19]
Adair et al.

[11] Patent Number: 4,478,641
[45] Date of Patent: Oct. 23, 1984

[54] EMBEDDING MATERIAL USEFUL IN PREPARING GLASS-CERAMIC PRODUCTS

[75] Inventors: Peter J. Adair, Boston, Mass.; Michael P. Hobczuk; Paul I. Kingsbury, both of Elmira, N.Y.; John W. Nelson, Painted Post, N.Y.

[73] Assignee: Corning Glass Works, Corning, N.Y.

[21] Appl. No.: 477,168

[22] Filed: Mar. 21, 1983

[51] Int. Cl.³ .................................................. C04B 11/00
[52] U.S. Cl. .................................. 106/110; 106/38.3; 106/38.9
[58] Field of Search .................. 106/110, 109, 38.3, 106/38.9

[56] References Cited

U.S. PATENT DOCUMENTS

| | | | |
|---|---|---|---|
| 2,283,611 | 5/1942 | Neiman | 106/110 |
| 2,607,969 | 8/1952 | Evans et al. | 106/110 |
| 3,069,278 | 12/1962 | Kimpel | 106/110 |
| 4,261,757 | 4/1981 | Mathieu | 106/110 |

Primary Examiner—Mark Bell
Attorney, Agent, or Firm—C. S. Janes, Jr.

[57] ABSTRACT

The instant invention relates to the development of an embedment material suitable for use in heat treating glass castings to convert them into glass-ceramic articles, whereby the shrinkage customarily experienced resulting from densification of the casting during conversion to a glass-ceramic is minimized and sound glass-ceramic articles of tight dimensional tolerances can be produced. The inventive embedment materials will:

(a) contain an inorganic component which is subject to an inversion accompanied with a large change in volume at a temperature below the set point of the glass-ceramic article;

(b) demonstrate a coefficient of thermal expansion equal to or no more than about $40 \times 10^{-7}/°C$. units greater than that exhibited by the glass-ceramic article;

(c) display a refractoriness sufficient to resist thermal deformation and slumping and be resistant to a phase change at the temperature employed to convert the glass casting to a glass-ceramic article; and (d) be inert to the glass and glass-ceramic.

One particularly suitable investment consists essentially, by weight, of 5-30% plaster of Paris and 70-95% leucite.

2 Claims, 6 Drawing Figures

EMBEDDING MATERIAL USEFUL IN PREPARING GLASS-CERAMIC PRODUCTS

BACKGROUND OF THE INVENTION

It has long been recognized in the field of glass-ceramics that, upon heat treating a precursor glass body to convert it into a glass-ceramic body, a relatively small, but nevertheless significant, shrinkage of the body customarily occurs due to densification taking place therein as crystals are developed and grown in situ. This phenomenon is illustrated in FIG. 1 which depicts a typical length-change curve with time and temperature exhibited by a precursor glass capable of being transformed via heat treatment into a glass-ceramic body. Thus, the AB portion of the curve reflects the thermal expansion manifested by the glass as it is heated to its transition temperature B. At that temperature (slightly above the annealing point of the glass) phase separation and/or nucleation is initiated in the glass. C designates the temperature at which crystal growth commences within the glass with consequent densification thereof. The segment CD represents the rapid shrinkage of the body as the temperature is raised to expedite crystallization therein, followed by a general leveling off as completion of the desired crystallization of the parent glass to a glass-ceramic body is accomplished. Typically, as is illustrated in FIG. 1, a crystallization hold or dwell period at a particular temperature is utilized to complete crystallization but that practice is not mandatory. All that is required is exposure to temperatures above C. It will be appreciated that with certain glass compositions a series of crystal phases may be developed as the temperature of the parent glass is raised. Accordingly, C represents the temperature at which growth of the desired crystal phase commences. DE indicates the thermal contraction of the glass-ceramic as it is cooled to room temperature. The obvious decrease in size experienced by the precursor glass body is an inherent concomitant of the densification occurring during the crystallization in situ thereof.

In most commercially-marketed glass-ceramic products, e.g., culinary ware, dinnerware, radomes, etc., the overall dimensional specifications are not so stringent but what a modest compensation for shrinkage by utilizing a parent glass body having dimensions slightly larger than the desired final product will suffice to satisfy the product needs. Where tight dimensional tolerances have been demanded, however, costly and time-consuming grinding or other machining techniques have been demanded. This shrinkage phenomenon has been especially worrisome in the recent practice of employing glass-ceramic materials in the preparation of dental restorations. As can well be appreciated, the fit of a dental construct is of utmost importance to the patient.

U.S. Application Ser. No. 373,617, filed Apr. 30, 1982 and entitled DENTAL PRODUCTS AND PROCESSES INVOLVING MICA COMPOSITIONS, now U.S. Pat. No. 4,431,420 discloses a process for the fabrication of dental tools, models, and constructs wherein the body thereof consists of a glass-ceramic having a composition within a narrowly-defined composition region to thereby yield material exhibiting the following six characteristics: (1) a visual appearance similar to that of tooth enamel; (2) inertness to chemicals encountered in an oral environment; (3) high mechanical strength and impact resistance to withstand the forces of mastication; (4) the capability of being processed via traditional laboratory techniques; (5) a coefficient of thermal expansion and a thermal conductivity similar to tooth enamel; and (6) the capability of being machined or otherwise mechanically shaped with relative ease, utilizing conventional metalworking tools, such as to permit the ready fashioning of the body to a desired anatomical configuration. Compositions providing that matrix of chemical and physical properties are reported as consisting essentially, expressed in terms of weight percent on the oxide basis, of $K_2O$: 10–18
MgO: 14–19
$SiO_2$: 55–65
$Al_2O_3$: 0–2
$ZrO_2$: 0–7
F: 4–9 wherein SrO and BaO may optionally be substituted for up to 50% of the $K_2O$ content on the molar basis. To secure the best chemical durability and resistance to food staining, the preferred compositions will contain 1–9% $Al_2O_3$+$ZrO_2$, with the most preferred including at least 0.5% $Al_2O_3$ and/or at least 2% $ZrO_2$.

The inventive method disclosed contemplated four general steps:

(1) a batch for a glass of a desired composition is melted;

(2) the melt is simultaneously cooled and shaped to form a glass body having an intermediate configuration with at least one selected surface of a specified conformation;

(3) the glass body is heat treated at about 1050°–1150° C. to cause the in situ growth of tetrasilicic fluormica crystals, thereby converting the glass body to a glass-ceramic body containing tetrasilicic fluormica as the predominant crystal phase; and thereafter (4) the glass-ceramic body is machined or otherwise formed to produce selected surfaces of the desired final geometry.

As is observed in that disclosure, the shaping of the glass body having an intermediate configuration is carried out utilizing standard investment casting techniques. Hence, as is explained therein, the conventional investment casting process comprises:

(a) pressing a soft impression material against a dental surface to establish a shape and solidifying the shape to form an impression;

(b) filling said impression with dental stone material and solidifying the dental stone material to from a model;

(c) preparing a wax pattern from said model;

(d) placing the pattern in an investment casting slurry on a sprue that extends from the pattern to a surface of the slurry and solidifying the slurry to form a mold;

(e) removing the sprue and the pattern from the mold;

(f) melting a glass preform of a desired composition;

(g) heating the mold to an elevated temperature but below the melting temperature of the glass preform; and then (h) casting the melt into the mold to form a glass body having an intermediate configuration.

In accordance with an illustrative working example, the glass body was removed from the mold and subsequently heat treated to convert it into the desired glass-ceramic body.

Further research has indicated that conducting the heat treating of glass preform outside the mold to effect crystallization in situ thereof results in such a high degree of distortion therein due to thermal slumping and shrinkage as to render the product virtually useless in many instances. Therefore, as a solution to the problem, crystallization of the glass preform was undertaken with the preform contained within a stable ceramic embedment. It was believed that the embodiment would prevent distortion due to thermal slumping and inhibit shrinkage. Unfortunately, the problem was not so simple that it could be readily solved with the commercially-available materials.

The goal of the dental laboratory is to produce finished castings that are about 5000-10,000 PPM (parts per million), equivalent to 0.5-1%, greater than the size of the die from which they were molded. This is accomplished by balancing the thermal expansions and shrinkages of the material being cast and the investment. The currently-marketed investment materials were formulated with metals in mind. However, the thermal contraction manifested by the metals employed in dental constructs is less than the sum of the thermal contraction and crystal densification which the glass-ceramic compositions disclosed in Ser. No. 373,617 undergo. That difference is sufficiently large to preclude the glass-ceramic castings from fitting on their respective dies.

One method for limiting the effect, but not the fact, of body shrinkage when the glass is crystallized in situ ("cerammed") to a glass-ceramic was attempted by filling the cavity of the casting with a commercially-available, rigid refractory material which impeded the inherent radial shrinkage of the casting. Densification of the casting still occurred and the concomitant stretching thereof resulted in a slight reduction in wall thickness (note FIG. 2), frequently accompanied with cracking and/or breaking. The investment employed, marketed by Whip-Mix Corporation, Louisville, Ky. under the name Hi-Heat Soldering Investment, consists of a mixture of quartz and plaster of Paris with added setting and shrinkage agents. Analysis of the fracture character indicated that the cracking took place as the crystallized body was cooled to room temperature after the ceramming treatment. This analysis is discussed below.

FIG. 1 illustrates that the precursor glass is at a temperature above its annealing point when it is subjected to the crystallization heat treatment. Accordingly, the viscosity of the glass at such temperature is sufficiently low that no significant stress can be built up. Therefore, the cracking and/or breakage encountered must occur during heating of the glass or cooling of the glass-ceramic.

As is indicated in FIG. 1, the densification (with concomitant shrinkage) experienced as the glass is converted into a glass-ceramic takes place in concert with the development of crystallization. Accordingly, the rate of densification is directly related to the rate of crystal development which, in turn, is a function of the heat treating temperature. As is manifest in FIG. 3, the breakage almost always involves a crack running from the margin to the top of the casting, customarily along one side. The crack is closed, thereby implying that the casting did not go through a plastic (softening) stage after cracking. Furthermore, the fracture surface does not exhibit the skin which commonly develops on the exposed surfaces of the castings during the crystallization treatment. Consequently, the crack was self-evidently produced during cooling of the glass-ceramic.

As observed, the commercial investment material utilized consisted substantially of quartz and plaster of Paris ($CaSO_4.\frac{1}{2}H_2O$). When mixed with water, the plaster is hydrated to monoclinic gypsum ($CaSO_4.2H_2O$). When fired, water is driven off and water-soluble hexagonal anhydrite ($CaSO_4$) is formed. At a temperature in the vicinity of 350° C., the hexagonal $CaSO_4$ is transformed into a slightly water-souble orthorhombic form. This transformation is accompanied with a density change of about 13%, which corresponds to a linear shrinkage of approximately 4.3%. Because of that intrinsic shrinkage of $CaSO_4$, quartz is added thereto to compensate therefor. Quartz is subject to an inversion at 573° C. which is accompanied by a large increase in volume. The resultant phase, termed $\beta$-quartz, exhibits a coefficient of thermal expansion of essentially zero. FIG. 4 represents what are believed to be the thermal expansion characteristics of the commercial embedment material during the crystallization heat treatment (Curve I), along with the thermal expansion characteristics of a typical glass-ceramic of Ser. No. 373,617 (Curve II).

With the glass compositions of Ser. No. 373,617, the annealing points thereof range between about 600°-625° C., the onset of crystallization occurs at about 650°-700° C., and the completion of the desired tetrasilicic fluormica crystallization takes place at about 1050° C. FIG. 4 demonstrates that the commercial investment shrinks somewhat at about 1000° C., i.e., below the temperature utilized for crystal growth of the glass compositions, this shrinkage resulting from sintering and consolidation of the material. Accordingly, if the annealing points are deemed to effectively represent the setting points of the glasses, then, when the cavity of a crown construct casting is completely filled with an embedment material, the critical inside dimension of the construct will conform to the geometry of the embedment as the construct is heated to effect crystallization thereof. Upon cooling from the crystallization temperature region, the glass-ceramic construct will continue to accommodate itself to the embedment until the setting point of the glass-ceramic (about 775°-825° C.) is reached and the casting can begin to support stress.

Unfortunately, because of the wide disparity existing between the coefficients of thermal expansion of the embedment material and the glass-ceramics of Ser. No. 373,617, the casting is placed in tension (the shaded portions of FIG. 4 indicate when the casting is in tension) and cracking of the construct occurs during cooling over the range of temperatures between about 800°-500° C.

Therefore, the principal objective of the instant invention is to develop materials operable as embedments for heat treating glass castings, whereby the shrinkage customarily experienced resulting from densification of the body as the glass is converted into a glass-ceramic will be minimized and glass-ceramic articles of tight dimensional tolerances can be produced.

The conventional method employed in dental laboratories to compensate for shrinkage inherent in the making of alloy restorations, viz., adjusting the investment liquid:power ratio, is not applicable with glass-ceramic materials. That is, the magnitude of the size change that can be effected by that technique is not adequate with the compositions disclosed in Ser. No. 373,617. Accordingly, a specific objective of the present invention is to devise an embedment material which will permit the preparation of glass-ceramic dental constructs, models, and tools which are free from cracking and/or breakage via the heat treatment of glass castings having compositions disclosed in Ser. No. 373,617.

PRIOR ART

The use of glass-ceramic materials for forming dental crowns and inlays was suggested in "Advances in Dental Ceramics", W. T. MacCulloch, *British Dental Journal,* Apr. 16, 1968, pages 361-5. The author discussed the use of a metal phosphate as a nucleating agent and fabricated a tooth from a glass-ceramic composition within the $Li_2O$-$ZnO$-$SiO_2$ field. MacCulloch also disclosed that, through the utilization of silver as the nucleating agent for his compositions, the parent glasses exhibited photosensitive behavior such that, through differential exposure of the glass with ultraviolet radiation, differences in crystallization could be induced in the materials, thereby simulating the polychromatic effect of natural teeth. The only composition data supplied by the author comprised the single reference to $Li_2O$-$ZnO$-$SiO_2$ glass-ceramics with no details as to operable quantities of each component. No description of investment materials was provided.

U.S. Pat. No. 4,189,325 discloses the utility of glass-ceramic bodies for dental restorations. The compositions claimed therefor consisted essentially, expressed in terms of mole percent on the oxide basis, of 25-33% $Li_2O$, 1-10% $CaO$, 0.5-5% $Al_2O_3$, and 52-73.5% $SiO_2$ to which were added 0.003-0.01% by weight Pt and 0.2-2% by weight $Nb_2O_5$ as nucleating agents. No data with respect to the identity of the crystals are present therein, but the compositions cited are self-evidently quite far removed from those of Ser. No. 373,617. The patentees observed that commercially available investment dental laboratory molds, i.e., the same types of molds currently used in dental laboratories for making cast alloy dental alloys, were operable with their compositions. While noting the occurrence of shrinkage during crystallization of the precursor glass to a glass-ceramic, the patentees asserted that such could be compensated for by proper adjustment of the investment liquid:powder ratio.

BRIEF DESCRIPTION OF THE DRAWINGS

To promote a more complete and clearer understanding of the nature and objective of the instant invention, reference is made to the following detailed description thereof, which is to be read in light of the accompanying drawings, wherein.

SUMMARY OF THE INVENTION

Figure 1:
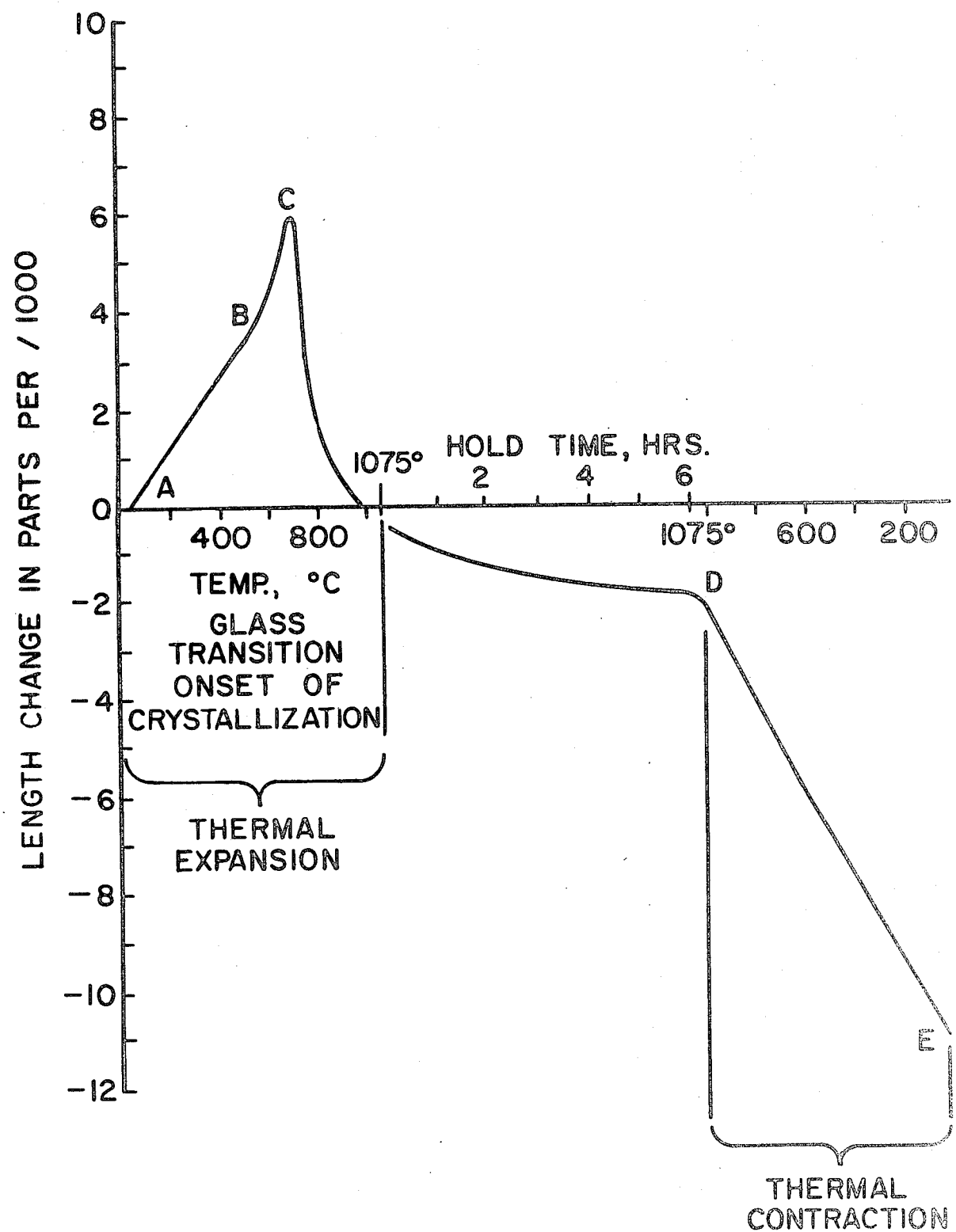
FIG. 1 depicts a typical length-change curve with time and temperature exhibited by a precursor glass capable of being converted into a glass-ceramic body.
Figure 4:
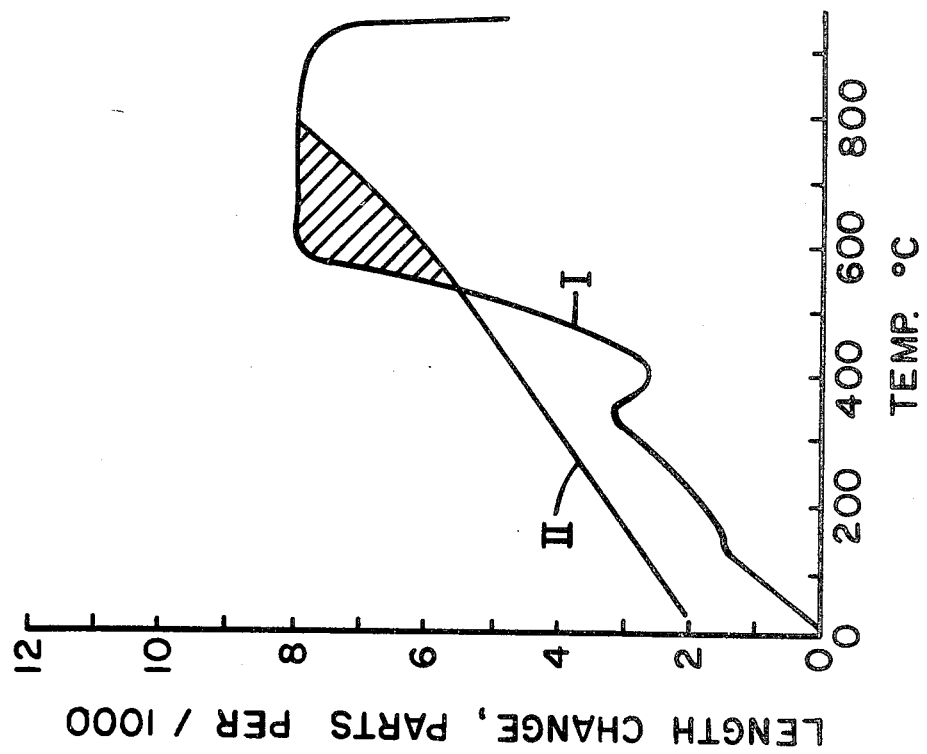
FIG. 4 illustrates the thermal expansion characteristics of a commercially-marketed investment when heated, and those of a typical glass-ceramic disclosed in Ser. No. 373,617.
Figure 2:
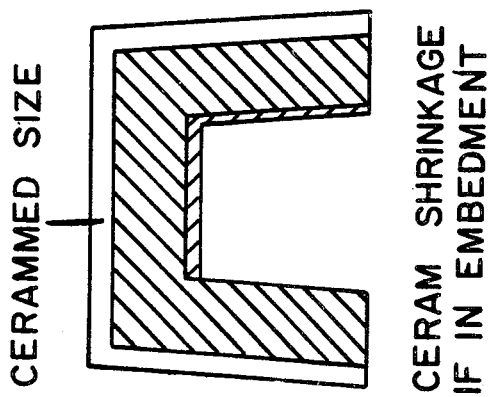
FIG. 2 is a schematic representation of the shrinkage experienced by a glass casting having a cavity therein filled with rigid refractory material when heat treated to convert the glass to a glass-ceramic.
Figure 3:
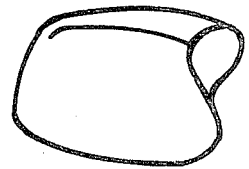
FIG. 3 is a schematic representation of a crack appearing in a glass-ceramic crown construct prepared via heat treatment in an embedment material not conforming to the requirements of the present invention.

We have determined that the above recorded principal objective of the instant invention can be achieved via the use of an essentially inorganic embedment material conforming to the following requirements:

(a) it will contain an inorganic component which is subject to an inversion accompanied with a large change in volume at a temperature below the set point of the glass-ceramic, said inorganic component being present in an amount sufficient to impart an increase in volume to the embedment, prior to the sintering and consolidation thereof, of greater magnitude than that of the precursor glass casting resulting from the thermal expansion thereof;

(b) the coefficient of thermal expansion of the embedment material will be relatively compatible with that of the final glass-ceramic body; i.e., the coefficient of thermal expansion of the embedment material will be equal to or not more than about $40 \times 10^{-7}$/°C. units greater than the glass-ceramic;

(c) the refractoriness of the embedment material must be sufficiently high to resist thermal deformation, slumping, or phase changes at the temperatures required for heat treating the glass casting to crystallize it in situ; and (d) the embedment material must be inert to the glass and the glass-ceramic to preclude sticking and/or reaction during heat treatment of the glass.

Those characteristics enable the embedment to support the precursor glass casting throughout the crystallization step and very little stress will be set up in the final glass-ceramic article as it is cooled below the set point thereof. Consequently, following a measurement of the coefficient of thermal expansion of the precursor glass, the temperature required to convert the precursor glass into a glass-ceramic, the coefficient of expansion of the glass-ceramic, and the set point of the glass-ceramic, one will seek to design an embedment material which will demonstrate the above four criteria, and will yield sound products wherein shrinkage of internal dimensions commonly observed in the transformation of a glass to a glass-ceramic is minimized.

The above-noted specific objective, viz., the preparation of crack-free dental constructs, models, and tools from parent glass compositions described in and heat treated in accordance with Ser. No. 373,617, can be accomplished by utilizing an embedment which contains an inorganic component subject to an inversion accompanied with a large change in volume at a temperature below about 775°-825° C., the embedment exhibits a coefficient of thermal expansion not greater than $70-90 \times 10^{-7}$/°C. by more than $40 \times 10^{-7}$/°C. units, and the embedment is capable of long term exposure to temperatures of about 1050°-1150° C. without thermal deformation or change of phase.

One operable embedment material consists essentially of leucite and plaster of Paris. Leucite is a potassium aluminum silicate having the general formula $K_2O \cdot Al$-

$_2O_3.4SiO_2$ which undergoes a phase transformation associated with a large increase in volume when heated to about 650° C. Leucite exhibits a melting point of about 1686° C. and the coefficient of thermal expansion (600°–1000° C.) of the high temperature phase of leucite is about $90-100 \times 10^{-7}$/°C. The glass-ceramics disclosed in Ser. No. 373,617 are prepared by heat treating the parent glass compositions at about 1050°–1150° and demonstrate set points between about 775°–825° C. and coefficients of thermal expansion (25°–300° C.) of about $70-90 \times 10^{-7}$/°C. Thus, embedments satisfying the criteria for the fabrication of crack-free dental restorations can be prepared from formulations consisting essentially, in weight percent, of about 5–30% plaster of Paris and 70–95% leucite. Where desired, minor amounts of conventional setting agents and fillers may be included.

Another operable embedment material comprises a narrow range of components within the ternary system $Al_2O_3$-cristobalite-plaster of Paris with the optional inclusion of leucite. $Al_2O_3$ demonstrates a melting point of about 2020° C. and a coefficient of thermal expansion (0°–300° C.) of about $85 \times 10^{-7}$/°C. Cristobalite, a polymorph of $SiO_2$, exhibits a melting point of about 1710° C., a sharp inversion at about 220° C. from the $\alpha$ to the $\beta$ phase which is accompanied with a large increase in volume, and a coefficient of thermal expansion over a range of temperatures above 220° C. in excess of $110 \times 10^{-7}$/°C. Satisfactory embedments for use with the glass-ceramic materials disclosed in Ser. No. 373,617 can be produced from compositions consisting essentially, in weight percent, of about 45–60% $Al_2O_3$, 25–35% cristobalite, 5–20% plaster of Paris, and 0–15% leucite. In like manner with the above-described leucite-plaster of Paris formulations, minor amounts of conventional setting agents and fillers may be included.

DESCRIPTION OF PREFERRED EMBODIMENTS

The following examples were carried out at the laboratory bench and must be deemed illustrative only and not limitative. It will be understood that the materials utilized will be at least as equally operable utilizing the more sophisticated apparatus of the commerical dental laboratory.

EXAMPLE 1

In order to investigate the thermal expansion characteristics of leucite-plaster of Paris embedment, a 10% by weight plaster of Paris, 90% by weight leucite (average particle size of 22 microns) mixture was made into a slurry with water (35 ml water and 100 grams solids) and poured into molds to yield bars having dimensions of about $4'' \times \frac{1}{4}'' \times \frac{1}{4}''$. After drying, the bars were cut into equal parts and the $2'' \times \frac{1}{4}'' \times \frac{1}{4}''$ sections then heated in the presence of a recording dilatometer at a rate of about 200° C./hour to 1075° C., held at that temperature for about one hour, and thereafter cooled to room temperature at about 200° C./hour. That heating schedule is quite applicable in producing glass-ceramic articles from the glass compositions of Ser. No. 363,617.

Figure 5:
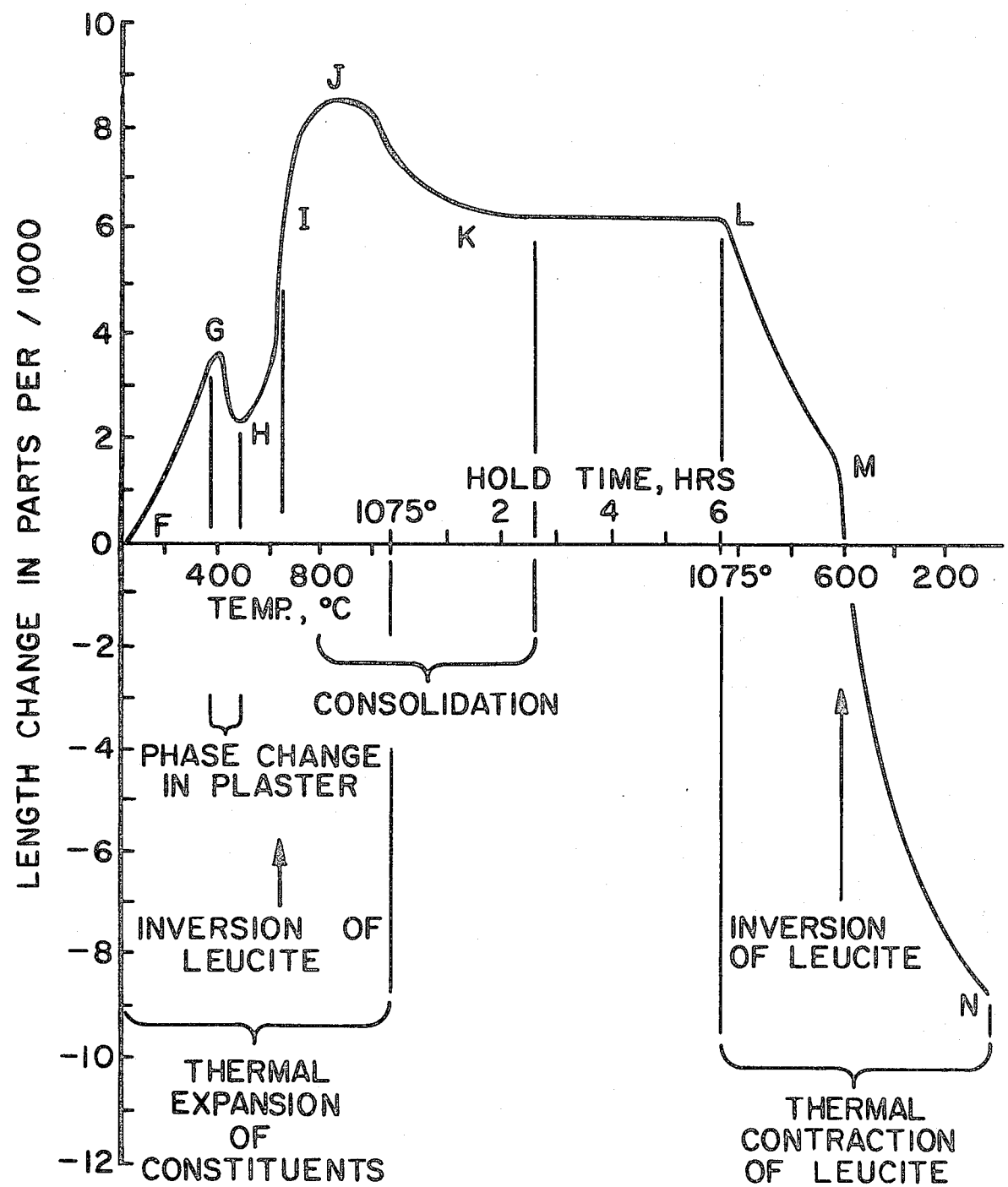
FIG. 5 provides a length-change curve with time and temperature displayed by an embedment material operable in the instant invention.

FIG. 5 represents an average length-change curve with time and temperature demonstrated by those bars. Thus, that segment of the curve designated FG indicates the thermal expansion of the embedment material as it is heated to about 350° C. At about 350° C., as has been explained earlier, hexagonal anhydrite is converted into the orthorhombic form, which transformation results in an increase in density and a linear shrinkage. That increase in density with concomitant shrinkage is reflected in that portion of the curve GH. Point I illustrates the temperature at which the leucite undergoes an inversion with an associated large increase in volume. Point J represents the maximum expansion experienced by the embedment material, that value reflecting a composite of the thermal expansion of the orthorhombic form of anhydrite and the high temperature form of leucite, plus the increase in volume resulting from inversion of the leucite. Segment JK illustrates the increase in density, with accompanying shrinkage, displayed by the material as the temperature is further raised in the manner necessary to convert the precursor glass to a glass-ceramic. That temperature also produces sintering and consolidation of the embedment with consequent shrinkage thereof. The relatively horizontal segment KL illustrates that the embedment will maintain a virtually constant geometry as the temperature is held at a particular temperature to complete the desired crystallization of the glass-ceramic. The LM portion of the curve reflects the contraction of the investment as the temperature is reduced to the inversion temperature M of leucite, with consequent decrease in volume. The segment MN designates the thermal contraction of the embedment as it is finally cooled to room temperature. The evident decrease in the size of the bars after firing is an inherent result of densification brought about through sintering and consolidation.

Thereafter, glass bars having dimensions of about $2'' \times \frac{1}{4}'' \times \frac{1}{4}''$ were prepared from a composition consisting essentially, expressed in terms of parts by weight on the oxide basis, of about $SiO_2$: 64.0
MgO: 11.9
$K_2O$: 14.4
$MgF_2$: 9.7
$ZrO_2$: 5.0

Figure 6:
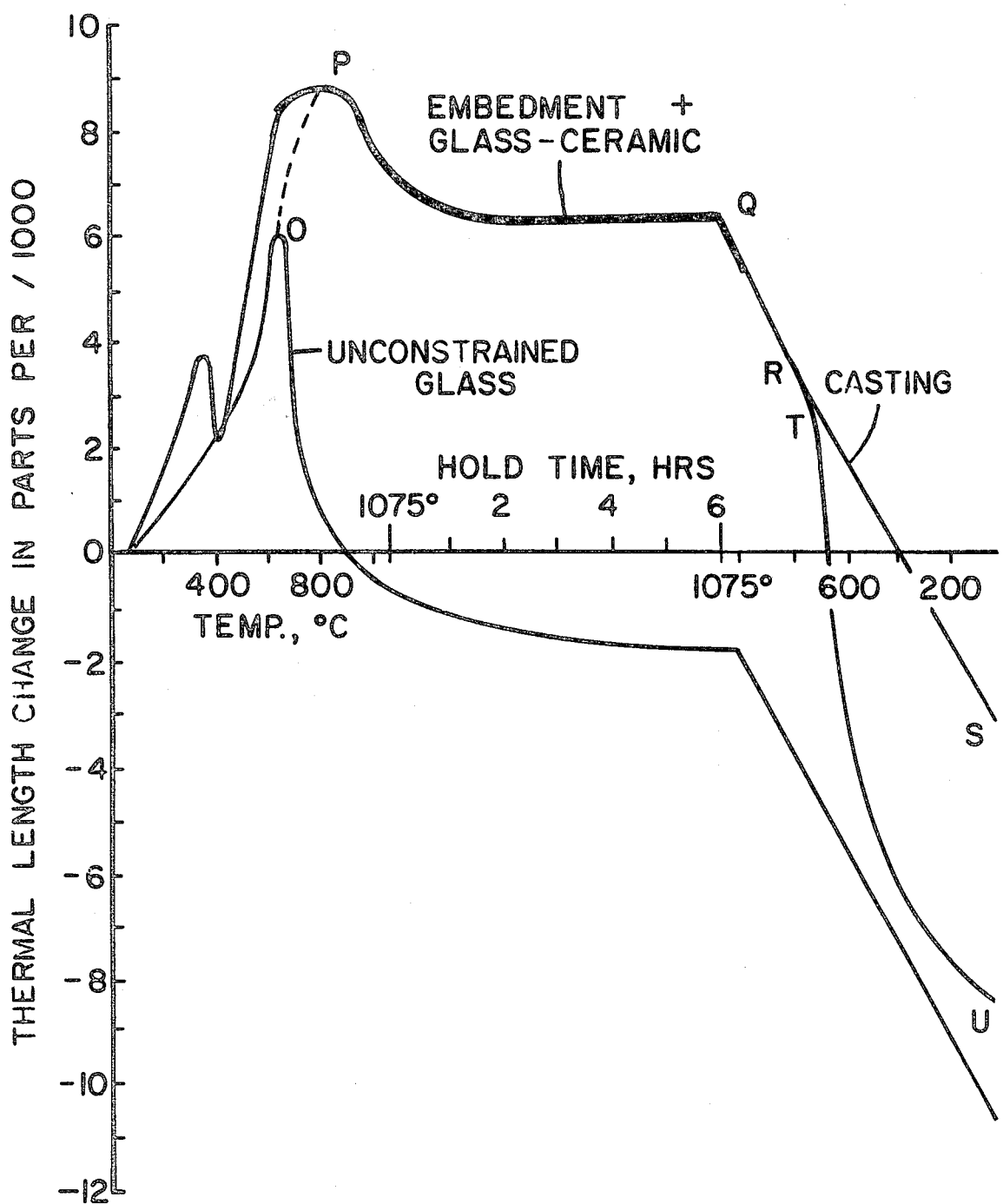
FIG. 6 sets forth a length-change curve with time and temperature demonstrated by a precursor glass material operable in the present invention and a length-change curve with time and temperature exhibited by the precursor glass and an inventive embedment material when maintained in contact with each other.

The bars were subjected to the same heat treatment as reported above for the bars of embedment material. The parent glass exhibited a set point of about 600° C. and a coefficient of thermal expansion of about $70 \times 10^{-7}$/°C. The resulting glass-ceramic demonstrated a set point of about 800° C. and a coefficient of thermal expansion of about $90 \times 10^{-7}$/°C. FIG. 6 depicts a length-change curve with time and temperature determined on unconstrained bars of glass when heated in the presence of a recording dilatometer.

FIG. 6 also illustrates the mechanism underlying the present invention. Thus, the curve bearing the legend "Embedment+Glass-Ceramic" represents a length-change curve with time and temperature exhibited when the precursor glass and embedment are maintained in contact with each other as, for example, when the cavity of a dental construct having the geometry of a crown is filled with embedment material and the crown then buried in the embedment. Dotted segment OP explains that the embedment prevents the glass from shrinking as crystallization takes place therein. Instead, the crystallizing glass body will be constrained by the embedment to follow the PQ portion of the curve as the desired crystallization is completed. The resulting glass-ceramic will be further restrained by the embedment as the two are cooled together from the crystallization temperature to the set point R of the glass-ceramic. That length of the curve PQR has been emphasized in FIG. 6 to indicate the combination of embedment and glass-ceramic through the reported temperature range.

RS delineates the thermal contraction of the glass-ceramic as it is cooled from the set point. The slope of that line is, of course, dependent upon the coefficient of thermal expansion of the glass-ceramic. T indicates the inversion temperature of the leucite and TU the thermal contraction of the investment as it is cooled to room temperature.

As was discussed above, the glass-ceramic will be under tension as it is cooled below the set point thereof. Because of the overall physical configuration of a crown and the relative thinness of the wall sections thereof, it is especially susceptible to cracking and breakage due to stresses built up as it is cooled below the set point of the glass-ceramic. Accordingly, the coefficients of thermal expansion of the glass-ceramic and the embedment must be relatively compatible. This need for compatibility is more critical under circumstances, as are present with the glass-ceramics formed from the compositions of Ser. No. 373,617, where the coefficient of thermal expansion of the glass-ceramic is quite high.

A comparison of the two curves drawn in FIG. 6, i.e., the extent of shrinkage experienced by the glass-ceramic constrained by the embedment during the crystallization heat treatment and that undergone by the unrestrained glass when converted into a glass-ceramic, clearly illustrates the significant benefit to be derived from the inventive process. Hence, the shrinkage of the constrained body will be no more than about one-half and, most frequently, must less than one-half that of the unconstrained glass.

EXAMPLE 2

A 50 gram batch of powdered leucite (40 grams) and plaster of Paris (10 grams) was thoroughly blended together in a bowl designed for use with paddle-type mechanical mixer. The leucite had an average particle size of about 22 microns. About 18 ml of tap water were added and the mixer operated for a sufficient length of time to insure complete wetting of the powder mixture (normally about 30 seconds). The moistened batch was subsequently mechanically spatulated under vacuum for about 30 seconds.

Thereafter, the cavity of a dental construct having the geometry of an anterior crown and being prepared from a glass having the composition reported above in Example 1 was filled with the water-batch slurry, being careful to avoid the inclusion of bubbles therein. A vibrator was utilized to secure removal of any bubbles generated.

About 10 ml of the slurry were deposited onto a paper towel resting on the pan of the vibrator. The crown was positioned margin up on the deposit of slurry and another few ml of slurry poured onto the crown. The vibrator was actuated for a few seconds and the filled crown allowed to air dry for about an hour.

The dried crown was then removed from the paper towel, introduced into an electrically-heated furnace, and subjected to a heat treatment schedule similar to that recorded above in Example 1. That is, the filled glass crown was heated at about 200° C./hour to 1075° C., held threat for about six hours, and cooled to room temperature at what has been termed "cooling at furnace rate". That practice contemplates simply cutting off the electricity to the furnace and allowing the furnace to cool with the crown retained therewithin. The rate of cooling averages about 200° C./hour.

Inspection of the fired crown, after removal of the embedment, evidenced a sound, highly crystalline body. No cracking of the shape was observed and shrinkage was less than 3000 ppm (parts per million) or 0.3%, thereby achieving the goal of the commercial dental laboratory.

(The use of leucite having an average particle size of about 22 microns enables the embedment to be removed from the fired crown with relative ease.)

EXAMPLE 3

A 100 gram batch consisting of about 25 grams of very finely-divided $Al_2O_3$ (at least one-half having particle diameters of less than 5.2 microns), about 25 grams of somewhat larger $Al_2O_3$ particles (at least one-half having diameters of less than 85 microns), about 30 grams cristobalite (at least one-half having particle diameters of less than 340 microns), about 10 grams powdered plaster of Paris, and about 10 grams powdered leucite (average particle size of about 22 microns) was thoroughly blended together in a bowl designed for use with a paddle-type mechanical mixer. About 36 ml of tap water were added and the mixer actuated for about 30 seconds to produce complete wetting of the powder mixture. Thereafter, the wetted batch was mechanically spatulated under vacuum for about 30 seconds. The particle sizes of the ingredients were adjusted to aid in making removal of the embedment from the subsequently formed construct relatively easy.

Thereafter, the practice for fashioning an anterior crown as described in Example 2 was followed. Inspection of the resulting fired crown, after removal of the embedment, found a sound, highly crystalline article. No cracking of the body was evident and shrinkage was less than 7000 ppm or 0.7%, again achieving the goal of the commercial dental laboratory.

We claim:

1. An embedment material for use with glass castings which are subsequently heat treated to convert the glass into a glass-ceramic, said glass casting consisting essentially, expressed in terms of weight percent on the oxide basis, of

| $K_2O$ | 10–18 | $Al_2O_3$ | 0–2 |
|---|---|---|---|
| MgO | 14–19 | $ZrO_2$ | 0–7 |
| $SiO_2$ | 55–65 | F | 4–9 | and said glass-ceramic exhibiting a coefficient of thermal expansion of about $70$–$90 \times 10^{-7}/°C.$, said embedment material, expressed in terms of weight percent, consisting essentially of 5–30% plaster of Paris and 70–95% leucite, or consisting essentially of 45–60% $Al_2O_3$, 25–35% cristobalite, 5–20% plaster of Paris, and 0–15% leucite, which material displays resistance to thermal deformation at a temperature between about 1050°–1150° C., demonstrates a coefficient of thermal expansion equal to or not more than $40 \times 10^{-7}/°C.$ units greater than that exhibited by said glass-ceramic, is subject to an inversion at a temperature below about 775°–825° C. accompanied with a change in volume of greater magnitude than that exhibited by said glass casting resulting from the thermal expansion thereof, and is inert to said glass and glass-ceramic, whereby the shrinkage customarily experienced during the densification of said casting as the glass is converted into a glass-ceramic is minimized and a sound glass-ceramic article of tight dimensional tolerances is produced.

2. An embedment material according to claim 1 wherein said shrinkage experienced during densification of said casting is no more than 0.75%.

* * * * *